Kühle et al.

United States Patent [19]

[11] 4,228,178
[45] Oct. 14, 1980

[54] COMBATING FUNGI WITH NOVEL N-SULPHENYLATED CARBAMOYL COMPOUNDS

[75] Inventors: Engelbert Kühle, Berg. Gladbach; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 960,396

[22] Filed: Nov. 13, 1978

[30] Foreign Application Priority Data

Dec. 7, 1977 [DE] Fed. Rep. of Germany ....... 2754492

[51] Int. Cl.² .................... A01N 9/22; C07D 209/48
[52] U.S. Cl. ................... 424/274; 260/326 H
[58] Field of Search ................... 260/326 H; 424/274

[56] References Cited

U.S. PATENT DOCUMENTS

| | | | |
|---|---|---|---|
| 2,553,770 | 5/1951 | Kittleson | 260/326 H |
| 3,639,471 | 2/1972 | Klauke et al. | 424/319 |
| 3,639,608 | 2/1972 | Adams et al. | 424/274 |
| 3,758,568 | 9/1973 | Phillips | 424/274 |
| 3,890,386 | 6/1975 | Kuhle et al. | 260/465 D |
| 3,980,693 | 9/1976 | Kuhle et al. | 260/465 D |
| 4,003,912 | 1/1977 | Franz | 424/274 |

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

N-Sulphenylated carbamoyl compounds of the formula

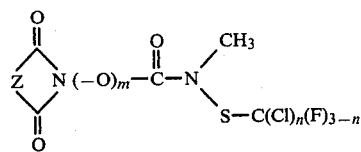

in which
Z represents two adjacent C atoms of a bifunctional lower aliphatic radical, of a cycloaliphatic radical or of an optionally substituted aromatic radical,
m denotes the number 0 or 1 and
n denotes the number 0, 1, 2 or 3,
which possess fungicidal properties.

7 Claims, No Drawings

COMBATING FUNGI WITH NOVEL N-SULPHENYLATED CARBAMOYL COMPOUNDS

The present invention relates to and has for its objects the provision of particular new N-sulphenylated carbamoyl compounds which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that N-trihalogenomethane-sulphenyl-dicarboximides have a fungicidal activity. Thus, for example, N-trichloromethanesulphenyl-tetrahydrophthalimide has been used in practice as a leaf fungicide in various crops for several years (see U.S. Pat. No. 2,553,770). This product is not always satisfactory with regard to its activity. Furthermore, N-sulphenylated carbamidoximes with a trihalogenomethane-sulphenyl radical act as fungicides; the fungicidal action is also not always adequate in the case of this class of compound (see in this context U.S. Pat. Nos. 3,890,386 and 3,980,693).

The present invention now provides the N-sulphenylated carbamoyl compounds of the general formula

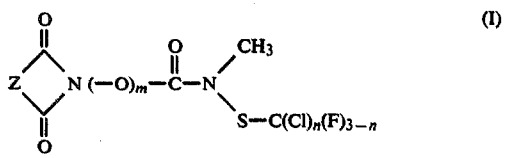

in which
Z represents two adjacent C atoms of a bifunctional lower aliphatic radical, of a cycloaliphatic radical or of an optionally substituted aromatic radical,
m denotes the number 0 or 1 and
n denotes the number 0, 1, 2 or 3.

Preferably, Z represents an aliphatic bifunctional radical with 2 to 4 carbon atoms, a cycloaliphatic five-membered or six-membered ring with 5 to 9 carbon atoms or an aromatic radical with 6 to 10 carbon atoms, which can be optionally substituted by nitro, chlorine, fluorine or a $C_1$-$C_4$ alkyl radical, and n represents the number 2 or 3.

It is to be described as surprising that the compounds according to the present invention have a higher fungicidal action than the compounds belonging to the state of the art. The new compounds found thus represent an enrichment of the art.

The present invention also provides a process for the preparation of an N-sulphenylated carbamoyl compound of the formula (I) in which an N-sulphenylated carbamic acid fluoride of the general formula

in which n has the meaning stated above, is reacted with a dicarboximide derivative of the general formula

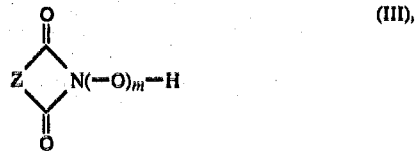

in which Z and m have the meanings stated above, in the presence of a diluent and of an acid-binding agent.

If phthalimide and N-(fluorodichloromethylsulphenyl)-methylcarbamic acid fluoride are used as starting materials, the course of the reaction can be represented by the equation which follows:

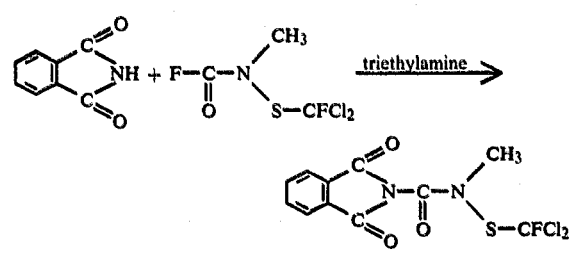

The N-sulphenylated methylcarbamic acid fluorides of the formula (II) are known (see DT-AS (German Published Specification) No. 1,297,095 and the corresponding U.S. Pat. No. 3,639,471).

Examples which may be mentioned of the dicarboximide derivatives of the formula (III) are the imides or oximides of maleic acid, succinic acid, itaconic acid or citraconic acid, and furthermore of dihydro-, tetrahydro-, hexahydro- and 4-methyltetrahydro-phthalic acid, of phthalic acid, 3-chlorophthalic acid, 4-nitrophthalic acid and 3-methylphthalic acid and of naphthalene-2,3-dicarboxylic acid. The compounds and their preparation are generally known.

Possible diluents are all the inert organic solvents, especially ethers, such as diethyl ether, tetrahydrofuran and dioxane; hydrocarbons, such as toluene; and chlorinated hydrocarbons, such as chloroform and chlorobenzene.

An acid-binding agent is added to the reaction mixture in order to bond the hydrogen fluoride formed during the reaction. A tertiary amine base, such as triethylamine, or an inorganic base, such as an alkali metal hydroxide or carbonate, is preferably used. The alkali metal salts of the dicarboxylic acid imides or oximides can also be reacted directly in an aqueous phase.

The reaction temperatures can be varied within a substantial range; in general, the reaction is carried out at about 0° to 100° C., preferably at about 20° to 50° C.

In carrying out the process, equimolar amounts of the reactants are generally used. In some cases it has proved advantageous to employ the sulphenylated methylcarbamic acid fluoride in a slight excess of up to about 20%.

The reaction mixture is worked up in the customary manner. The reaction products are in most cases crystalline compounds which, after adding water, can be separated off and if necessary redissolved and precipitated.

The active compounds according to the invention exhibit a powerful fungitoxic action. They do not damage crop plants in the concentrations required for combating fungi and bacteria. For these reasons they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which infect above-ground parts of plants or attack the plants through the soil, as well as against seedborne pathogens.

They develop a particularly good activity against parasitic fungi on above-ground parts of plants, such as, for example, against species of Phytophthora and against the apple scab causative organism (*Fusicladium dendriticum*). Furthermore, they exhibit a high activity against cereal diseases, such as against bunt of wheat and cereal rust.

As plant protection agents, the active compounds according to the invention can be used for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations are produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a substantial range. They are, in general, from 0.1 to 0.00001 percent by weight, preferably from 0.05 to 0.0001 percent.

In the treatment of seed, amounts of active compound of 0.001 to 50 g, especially 0.01 to 10 g, are generally employed per kilogram of seed.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi, which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the preparation of the novel compounds of the invention:

EXAMPLE 1

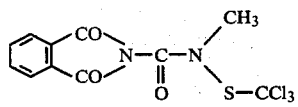

11 g (0.11 mol) of triethylamine were added dropwise to a solution of 14.7 g (0.1 mol) of phthalimide and 22.5 g (0.1 mol) of N-(trichloromethylthio)-N-methylcarbamic acid fluoride in 100 ml of dioxane at room temperature; no rise in temperature was observed during this addition. The solution was heated to 90° C. for 1 hour and then cooled, the solvent was distilled off in vacuo and ice-water was added to the residue. The residue crystallized out during this addition. After recrystallization from acetonitrile, 25 g of N-(N-methyl-N-trichloromethylthio-carbamoyl)phthalimide of melting point 155° to 157° C. were obtained.

EXAMPLE 2

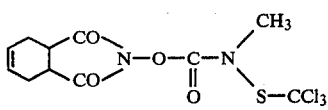

8.3 g (0.05 mol) of Δ⁴-tetrahydrophthal-oximide and 11.8 g (0.05 mol) of N-(trichloromethylthio)-N-methylcarbamic acid fluoride were dissolved in 80 ml of dioxane at 50° C. On adding 6 g of triethylamine dropwise, the temperature rose to 55° C. The reaction mixture was stirred at 60° C. for a further hour and, after cooling, water was added, whereupon the above product separated out as crystals. After drying, 16.5 g of a product of melting point 180° to 110° C. were obtained.

The compounds which follow, of the general formula

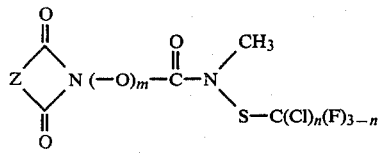

could be obtained in a manner corresponding to that described in the above examples:

TABLE

| Compound No. | Z | m | n | Melting point (°C.) |
|---|---|---|---|---|
| 3 | (benzene) | 0 | 2 | 100–101 |
| 4 | (cyclohexene) | 0 | 3 | 162–164 |
| 5 | (cyclohexene) | 0 | 2 | 129–133 |
| 6 | (cyclohexene-H) | 0 | 3 | 125–127 |
| 7 | (cyclohexene-H) | 0 | 2 | 105–106 |
| 8 | CH₂–CH₂ | 0 | 3 | 116–117 |

TABLE-continued

| Compound No. | Z | m | n | Melting point (°C.) |
|---|---|---|---|---|
| 9 | CH₂–CH₂ | 0 | 2 | 111–113 |
| 10 | (cyclohexene) | 1 | 2 | 92–93 |
| 11 | (cyclohexene) | 1 | 2 | 102–104 |
| 12 | (cyclohexene-H) | 1 | 3 | 117–119 |
| 13 | (cyclohexene-H) | 1 | 2 | 96–98 |

The fungicidal activity of the compounds of this invention is illustrated by the following biotest Examples.

EXAMPLE 3

Phytophthora test (tomatoes)/protective

Solvent: 4.7 parts by weight of acetone
Emulsifier: 0.3 parts by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18° to 20° C. After 5 days the infection of the tomato plants was determined.

The evaluation of the test showed that in particular compounds 2,3,4,5,6,7,8,11,12 and 13 according to the invention were superior to known comparison preparations (for example to N-methyl-N-fluorodichloromethylene-carbamic acid ester of benzhydroximic acid cyanide).

EXAMPLE 4

Fusicladium test (apple scab)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium* dendriticum) and incubated for 18 hours in a humidity chamber at 18° to 20° C. and at a relative atmospheric humidity of 100%.

The plants were then brought into a greenhouse again for 14 days.

15 days after inoculation, the infection of the seedlings was determined.

The evaluation of the test showed that in particular the compounds 3, 11 and 13 according to the invention were superior to known comparision preparations (for example to N-trichloromethanesulphenyl-tetrahydrophthalimide).

EXAMPLE 5

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20° C. and 100% atmospheric humidity.

After 10 days' dwell time of the plants at a temperature of 20° C. and 80 to 90% atmospheric humidity, the occurrence of rust pustules on the plant was evaluated. The more active the compound, the lower was the degree of rust infection.

The evaluation of the test showed that in particular compounds 5, 7 and 11 according to the invention were superior to known comparison preparations (for example to the zinc salt of ethylene-bis-dithiocarbamic acid).

EXAMPLE 6

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of Tilletia caries per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C. in a refrigerator.

The germination of the spores on the wheat grains, each of which was contaminated with about 100,000 spores, was subsequently determined microscopically. The smaller the number of spores which had germinated, the more effective was the active compound.

The evaluation of the test showed that in particular compounds 3 and 5 according to the invention were superior to known comparison preparations (for example to the zinc salt of ethylene-bis-dithiocarbamic acid and to the N-methyl-N-fluorodichloromethylthiocarbamic acid ester of benzhydroximic acid cyanide).

It will be appreciated that the instant specification and examples are set forth by way of illustration and not limitation, and that various modifications and changes may be made without departing from the spirit and scope of the present invention.

What is claimed is:

1. An N-sulphenylated carbamoyl compound of the formula

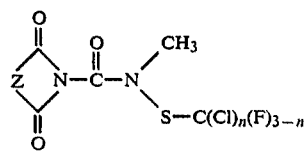

in which

Z represents phenyl, cyclohexyl or cyclohexenyl attached to the balance of the molecule through two adjacent C atoms, and n denotes the number 0, 1, 2 or 3.

2. A compound according to claim 1, in which said compound is N-(N-methyl-N-trichloromethylthio-carbamoyl)-phthalimide of the formula

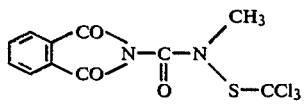

3. A compound according to claim 1, in which said compound is N-(N-methyl-N-dichlorofluoromethylthio-carbamoyl)-phthalimide of the formula

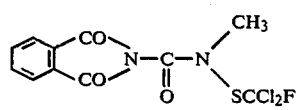

4. A compound according to claim 1, in which said compound is N-(N-methyl-N-dichlorofluoromethylthio-carbamoyl)-$\Delta^4$-tetrahydrophthalimide of the formula

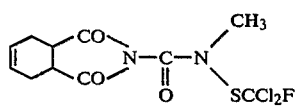

5. A fungicidal composition having as active ingredient a fungicidally effective amount of a compound according to claim 1 in admixture with a diluent.

6. A method of combating fungi which comprises applying to the fungi, or to a habitat thereof, a fungicidally effective amount of a compound according to claim 1.

7. The method according to claim 6, in which said compound is

N-(N-methyl-N-trichloromethylthio-carbamoyl)-phthalimide,

N-(N-methyl-N-dichlorofluoromethylthio-carbamoyl)-phthalimide, and

N-(N-methyl-N-dichlorofluoromethylthio-carbamoyl)-$\Delta^4$-tetrahydrophthalimide.

* * * * *